United States Patent [19]
Yamazaki et al.

[11] Patent Number: 5,531,789
[45] Date of Patent: Jul. 2, 1996

[54] SEALING SYSTEM OF AN ARTIFICIAL INTERNAL ORGAN

[75] Inventors: Kenji Yamazaki, Koganei; Toshio Mori, Chino, both of Japan

[73] Assignee: Sun Medical Technology Research Corporation, Nagano-ken, Japan

[21] Appl. No.: 360,411

[22] Filed: Dec. 21, 1994

[30] Foreign Application Priority Data

| Dec. 24, 1993 | [JP] | Japan | 5-354938 |
| Feb. 9, 1994 | [JP] | Japan | 6-050040 |
| Apr. 11, 1994 | [JP] | Japan | 6-107367 |

[51] Int. Cl.⁶ .................................. A61M 1/12
[52] U.S. Cl. ...................... 623/12; 623/3; 600/16
[58] Field of Search .................. 623/3, 11, 12; 600/16; 427/2.24, 2.3

[56] References Cited

U.S. PATENT DOCUMENTS

| 4,135,253 | 1/1979 | Reich et al. ................ 623/3 |
| 4,867,797 | 9/1989 | Thomasen et al. . | |
| 4,927,407 | 5/1990 | Dorman ..................... 623/3 |
| 5,145,333 | 9/1992 | Smith ........................ 623/3 |
| 5,147,388 | 9/1992 | Yamazaki .................. 623/2 |
| 5,275,580 | 1/1994 | Yamazaki .................. 600/16 |
| 5,324,647 | 6/1994 | Rubens et al. ............ 427/2.24 |

FOREIGN PATENT DOCUMENTS

| 0028122 | 5/1981 | European Pat. Off. . |
| WO93/21971 | 11/1993 | WIPO . |

*Primary Examiner*—Paul B. Prebilic
*Attorney, Agent, or Firm*—Nixon & Vanderhye

[57] ABSTRACT

An artificial internal organ, such as an artificial heart, comprising a pump unit through which blood circulates and a drive shaft for driving the pump unit, the drive shaft having a shaft sealing system thereon. The shaft sealing system is supplied with a sealing solution from a sealing solution chamber and a sealing solution bag. The sealing solution is formed mainly of a physiological saline, which is loaded with a protease or several kinds of aminopeptides. When blood gets into the shaft sealing system, it is prevented from coagulating by these admixtures. Although blood in the shaft sealing system of this type coagulates in a unique mechanism different from a conventional one, the protease and the aminopeptides never lose their effects even in such a unique situation.

5 Claims, 3 Drawing Sheets

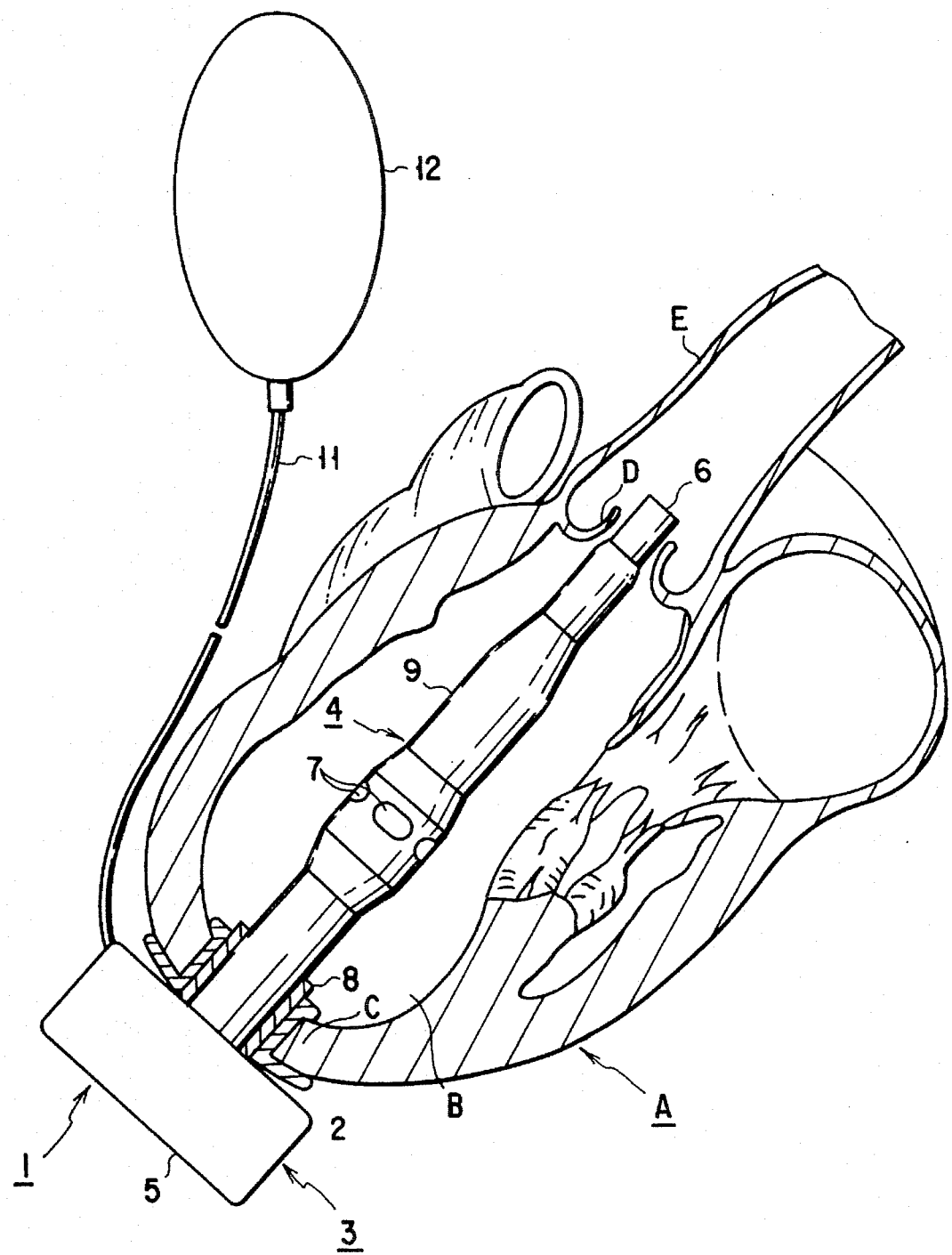
F I G. 2

SEALING SYSTEM OF AN ARTIFICIAL INTERNAL ORGAN

BACKGROUND OF THE INVENTION

Field of the Invention

The present invention relates to a sealing system for preventing blood from coagulating on moving parts in an artificial internal organ, such as an artificial heart or pump-oxygenator, in which blood is circulated and which is provided with a mechanical sealing system such as a shaft sealing system.

More specifically, the present invention relates to a sealing system in which a sealing solution is fed at a minute flow rate to that portion of the system which is in contact with blood, thereby preventing coagulation of blood in the system, the sealing solution being loaded with a substance capable of preventing the blood coagulation.

An artificial internal organ, such as an artificial heart, comprises a pump system for feeding blood and a drive system for driving the pump system. If the pump system is of an axial-flow type or centrifugal type, its propeller or impeller is rotated by means of a motor or the like through the drive shaft. In this arrangement, the drive shaft is provided with a sealing system for liquid-tight sealing, and is touched by blood.

Thus, blood gets into a space between moving parts of the shaft sealing system, and then coagulates therein. In some cases, therefore, the sealing system may suffer malfunction due to cohesion or the like, possibly stopping the rotating of the drive shaft.

In some conventional shaft sealing systems of this type, a sealing solution chamber is defined on one side, and is continually filled with a sealing solution so that blood can be prevented from getting into the system by the sealing solution. In general, a physiological saline is used as the sealing solution.

Even in this case, however, blood cannot be securely prevented from getting into the shaft sealing system. It is necessary, therefore, to provide means for preventing blood from coagulating in the system. These circumstances and requirements are common to pump-oxygenators and other artificial internal organs in which blood is circulated and which are provided with a mechanical sealing system, as well as artificial hearts.

In one such means for preventing blood coagulation in the sealing system, the sealing solution in the system is loaded with an anticoagulant such as heparin. This means cannot, however, produce any positive effect, since the anticoagulant action of heparin causes antithrombin III to suppress the activity of thrombin, thereby preventing fibrinogen in blood from changing into fibrin. However, blood in the shaft sealing system of this type, e.g., in a narrow gap between rotating and stationary members of a dynamic-pressure sealing system which doubles as a bearing, is subjected to a substantial shear deformation, and in some cases, may be locally heated to a high temperature of 50° to 70° C. Accordingly, blood may possibly coagulate in a mechanism different from the ordinary mechanism of blood coagulation. Thus, the blood coagulation cannot be effectively prevented by only suppressing the thrombin activity.

The present invention has been contrived in consideration of these circumstances, and a first object of the invention is to provide a sealing system in which an agent for preventing coagulation of blood is loaded into a sealing solution, thereby effectively preventing blood from coagulating in the sealing system. A second object of the invention is to provide a sealing system capable of securely preventing blood coagulation under various possible conditions. A third object of the invention is to provide a sealing system capable of maintaining a preventive effect against blood coagulation for the longest possible period of time.

SUMMARY OF THE INVENTION

In order to achieve the above object, a sealing system according to the present invention comprises means for feeding a sealing solution to moving parts of the sealing system. The sealing solution is loaded with at least one of proteases or aminopeptides.

The protease serves to cut coagulated fibrin bonds, thereby decomposing fibrin. The aminopeptide inhibits the process of polymerization of derivatives from fibrinogen with fibrin molecules. This action can securely prevent coagulation of blood in the sealing system which may otherwise occur in a mechanism different from the conventional one under special conditions, including a substantial shear deformation, high temperature, etc.

According to a preferred embodiment of the present invention, the protease is subtilisin or an enzyme selected among a group of enzymes similar to subtilisin. These enzymes have a positive proteolytic effect and a long life period for activity in a solution. These features are particularly effective for the case of an artificial internal organ, such as an implant-type artificial heart, in which the sealing solution cannot be easily resupplied or replaced.

According to another preferred embodiment of the invention, the sealing solution is loaded with a protease secreted by a thermoduric bacterium, e.g., thermolysin secreted by B-thermoproteolyticus. Proteases secreted by thermoduric bacteria have a working temperature as high as, e.g., 70° to 80° C., and can effectively act even though the interior of the sealing system is locally heated to high temperature. These proteases can maintain their effectiveness for a long period of time as long as the ambient temperature is substantially as high as bodily temperature. These features are expressly favorable for the aforesaid implant-type artificial heart.

According to still another preferred embodiment of the invention, the aminopeptide is a polypeptide formed of four amino acids, glycine, proline, arginine, and proline. The aminopeptide of this composition can effectively block polymerization of the γ-chain C-terminal receptors of fibrin monomers, thereby effectively preventing fibrin polymerization.

According to the present invention, the sealing solution is loaded with one or more of the aforementioned substances, whereby the coagulation of blood in the sealing system can be prevented securely.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a view showing the artificial heart of FIG. 1 implanted in the human body.

DETAILED DESCRIPTION OF THE PREFERRED EMBODIMENTS

Figure 1:
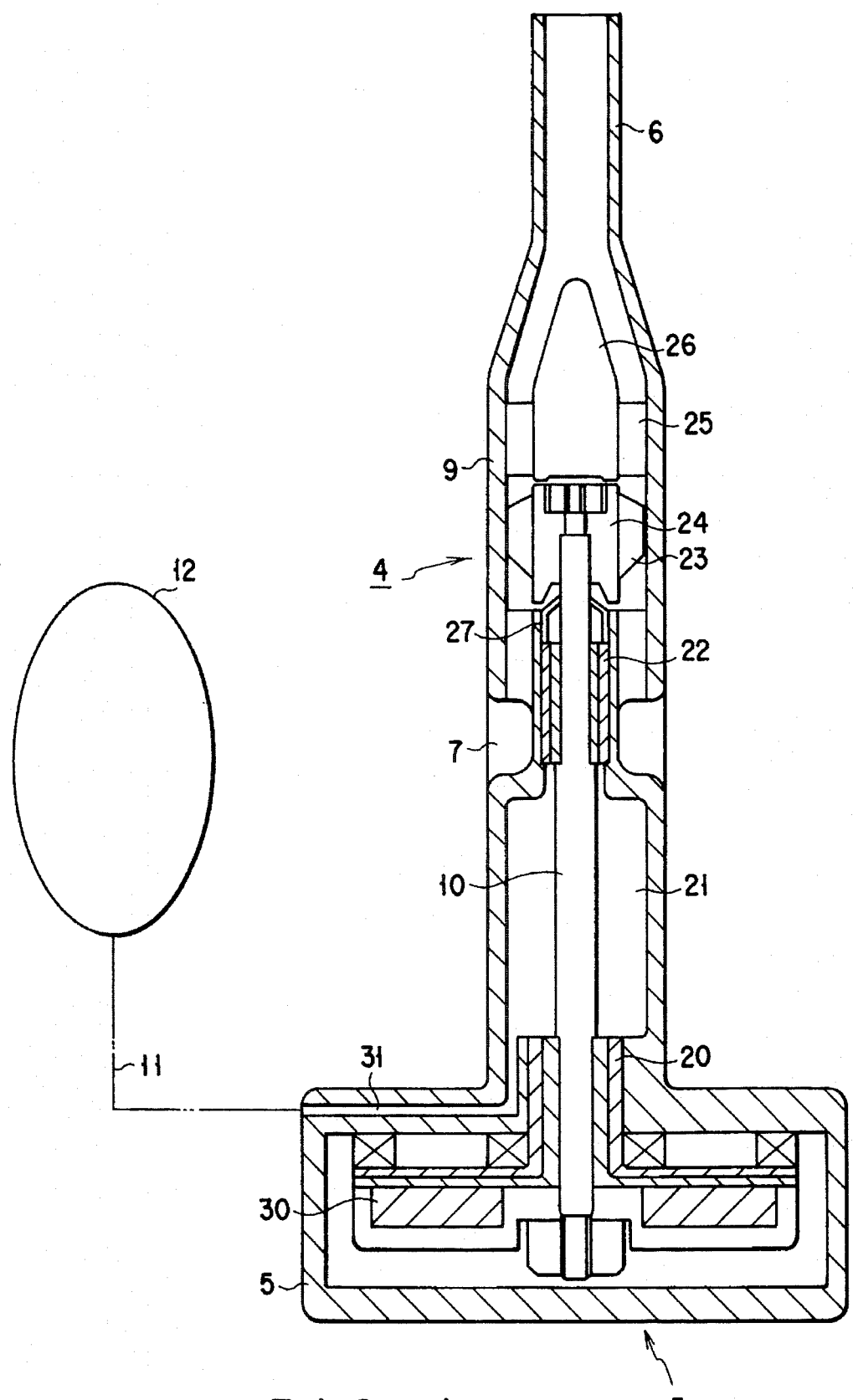
FIG. 1 is a longitudinal sectional view of an implant-type artificial heart according to one embodiment of the present invention.

The following is a description of the mechanism of coagulation of blood in a sealing system which constitutes the base of the present invention.

Fibrinogen is a coagulated protein with a molecular weight of 340,000 contained in blood, and is changed into fibrin by the action of thrombin in blood. Thrombin specifically transects Gly-Arg (glycine-arginine) bonds at the N-terminals of the A-α and B-β chains of fibrinogen. Thereupon, fibrinogen separates into fibrin monomers and fibrinopeptides A and B. A newly exposed A-α chain stump is complementally polymerized with a receptor on the D-domain. Moreover, the C-terminals of the γ chains are cross-linked by the action of thrombin and coagulation factors XIII, whereupon a stable fibrin bundle is obtained.

An experiment was conducted on the mechanism of fibrinogen coagulation in a small-sized unidirectional dynamic-pressure bearing (3 mm (φ)×10 mm (L)) of ceramics in a manner such that the bearing was rotated at high speed (8,000 to 10,000 rpm) in blood plasma. Since grooves with a depth of 4 μm for external circulation of a liquid in a gap are formed on the sliding face of a rotor of the unidirectional dynamic-pressure bearing, fibrinogen molecules subjected to a great shearing force in the bearing are forced out. Thereupon, the fibrinogen molecules can be checked for change in the bearing by examining the components of the blood plasma.

After the experiment was started, samples were extracted at regular time intervals, and their respective fibrinopeptide-A concentrations were compared with that of a control. As a result, those blood plasmas which were subjected to a great shearing force exhibited fibrinopeptide-A concentrations four to eight times as high as that of the control. This indicates that the Gly-Arg bonds at the N-terminals of the A-α chains of fibrinogen, which should originally be fragmented by the action of thrombin, were divided by physical effects (shearing force and heat).

It was confirmed, moreover, that macroscopically observable fibrin fibers were formed in the blood plasma. This fact indicates that a large number of fibrin monomers were formed having normal E- and D-domains which can be polymerized with other fibrin molecules.

The bearing cohered and stopped in 60 to 90 minutes. The sliding face of the bearing is covered by thermally denatured plasma protein. Based on these experimental results, the mechanism of coagulation of blood in the bearing can be thought following. The fibrinopeptide A is transected from the A-α chain of fibrinogen by the great shearing force and heat in the bearing, whereupon fibrin monomers are produced. The fibrin monomers are automatically polymerized with one another by the action of electric charges, thereby forming fibrin dimers and trimers with the progress of the polymerization, the viscosity and frictional resistance of the liquid in the bearing increase, so that generation of heat is augmented. When the temperature in the bearing is increased to 55° C. or more by this increase of viscosity and frictional heating, the plasma protein is coagulated by thermal denaturation, whereupon the bearing completely coheres at last.

In the coagulation of blood in the bearing, as described above, the transection of the fibrinopeptides is caused by physical effects, such as heat and shearing force, so that the cohesion of the bearing cannot be prevented by thrombin inhibition. The coagulation of blood in the bearing is believed to be attributable to degenerative coagulation of of blood protein components by heat. Although various sealing systems for preventing the blood components from getting into the bearing have conventionally been developed, none of them are satisfactory yet.

The present invention is based on a point of view that the coagulation of blood cannot be prevented by the conventional method which utilizes thrombin inhibition under the aforesaid special conditions in the sealing system.

A first feature of the present invention lies in the use of decomposition of protein as a method for preventing coagulation, besides the aforesaid thrombin inhibition. The decomposition of protein can securely prevent the coagulation of blood without being influenced by the aforementioned mechanism of the blood coagulation. A protease (proteolytic enzyme) is used for the decomposition of protein plasmin for use as a thrombolytic agent is conventionally known as an example of the protease. The life period of the enzyme activity of plasmin in a solution is about 90 minutes, which is too short for the prevention of the blood coagulation in a sealing system, such as the one according to the present invention. In the case of an implant-type artificial heart, in particular, a replenishing bag for a sealing solution sometimes may be also implanted in the body. Thus, the resupply or replacement of the sealing solution is not easy, and an enzyme with a long half-life period for activity is needed.

In consideration of these circumstances, according to the present invention, the sealing solution, which is formed mainly of a physiological saline, is loaded with subtilisin or at least one of enzymes which are similar to subtilisin. Subtilisin and the group of enzymes similar to subtilisin have a wide variety of action characteristics and a positive proteolytic effect. Also, the life period of their enzyme activity in a solution is very long, ranging from 14 days to 21 days. Thus, these enzymes fulfill requirements for an anti-coagulant for a sealing system of an artificial internal organ.

Proteases which fulfill those requirements include, besides the aforesaid ones, chymotrypsins A, B and C, acrosin, elastase, aspergillus alkaline proteinase, papain, bromelain, yeast proteinase, pronase, furin, PC-1, PC-2, PC-4, PACE-4, etc. Use of these admixtures produces the same effects as aforesaid.

Preferably, the aforementioned proteases should be ones which are secreted by thermoduric bacteria. These thermoduric bacteria are bacteria which are alive at too high a temperature for the survival of ordinary bacteria, and are found in hot-spring water of 70° to 80° C. The optimum working temperature of the proteases secreted from the thermoduric bacteria is within a high temperature range of, e.g., 70° to 80° C.

In the gap between the shaft and bearing of the sealing system, such as a shaft sealing system, as mentioned before, the sealing solution and blood are subjected to a substantial shear deformation. With the progress of the polymerization of the fibrin monomers in the gap, moreover, the viscosity of the solution increases, and in some cases, may be locally heated to a high temperature of 50° to 70° C. by the substantial shear deformation. In such a situation, ordinary proteases lose their activity, and cannot act effectively. However, the aforesaid proteases secreted by the thermoduric bacteria can act properly at such a high temperature, thereby preventing the coagulation of blood.

Moreover, the proteases secreted by the thermoduric bacteria are preferred because they can maintain their activity at bodily temperature, e.g., temperature of 36° to 40° C., for a month or longer period of time.

Thermolysin, which is secreted by B-thermoproteolyticus, is an applicable example of the proteases secreted by the thermoduric bacteria. Other proteases of this type include caldolysin secreted by thermus T-351, aqualysin secreted by thermus aquaticus, protease secreted by B-caldolyticus, protease secreted by *streptomyces rectus* var proteolyticus, protease secreted by *T-caldophilus sp* n strain GK24, etc. These proteases can produce the same effects.

A second feature of the present invention lies in that an aminopeptide is loaded into the sealing solution. As mentioned before, the mechanism of the coagulation of blood in the sealing system is a unique one different from the conventional one. In a final stage, however, the fibrin monomers formed by shear deformation or heat are polymerized as fibrin fibers are formed. If a high-concentration aminopeptide exists in the solution, in this case, the polymerization of the fibrin monomers is inhibited, and the formation of the fibrin fibers is prevented. Although this action differs from the action of the aforementioned proteases, these actions resemble each other in being effective even in the case where blood coagulates in a unique mechanism.

An example of this aminopeptide may be formed of glycine, proline, and arginine. The aminopeptide with this composition can effectively block the polymerization of the C-terminal receptors of the γ chains of the fibrin monomers, thereby effectively preventing the polymerization of the fibrins.

The N-terminals of the transected A-α chains of the fibrinopeptide A have an amino acid sequence, Gly (glycine)-Pro (proline)-Arg (arginine)-Val (valine)-Glu (glutamic acid)-Arg (arginine) . . . . Those portions of this sequence which are complementally polymerized with the γ-chain C-terminals consist of first three amino acids, Gly (glycine), Pro (proline), and Arg (arginine), individually.

The γ-chain C-terminal receptors, polymerized regions of the fibrin monomers, can be competitively blocked by loading a shaft cleaning fluid with the aminopeptide with the sequence Gly-Pro-Arg . . . .In contrast with this, the polymerized regions of the A-α-chain N-terminals can be blocked by means of a γ-chain C-terminal [His (histidine)-His (histidine)-Leu (leucine)-Gly (glycine)-Gly (glycine)-Ala (alanine)-Lys (lysine)-Gln (glutamine)-Ala (alanine)-Gly (glycine)-Asp (asparagine)-Val (valine) (γ400 to 411)]. These aminopeptides serve to prevent the polymerization of the fibrins and restrain the generation of frictional heat by sliding motion in the bearing, thereby preventing the coagulation attributable to the thermal denaturation of the plasma protein.

Substantially perfect competitive blocking of the polymerized regions requires use of aminopeptides with a molar concentration one hundred times that of the fibrinogen molecules in the bearing.

It is to be understood that the aforementioned proteases and aminopeptides can be used suitably in combination with one another. For example, the protease and other proteases secreted by thermoduric bacteria, having different activity life periods and working temperature ranges, are suitably combined so that necessary functions can be maintained for required periods of time.

The proteases have a function to decompose the already formed fibrin fibers and the like, while the aminopeptides have a function to inhibit the formation of the fibrin fibers. Thus, synergism can be obtained by combining these functions.

Referring now to FIGS. 1 and 2, an artificial heart according to the present invention will be described. This artificial heart is implanted in the heart and the body as it is used. Since a sealing solution bag for the artificial heart is also implanted in the body, the resupply or replacement of the sealing solution is not easy. Since the whole apparatus size is small, moreover, the sealing system is also small-sized, so that the sealing solution or blood in the sealing solution are bound to undergo a substantial shear deformation or local heat build-up. Accordingly, this artificial heart, among other ones, are subject to the strictest conditions for the prevention of blood coagulation in the sealing system.

In FIGS. 1 and 2, numeral 1 denotes a main body of the artificial heart. As shown in FIG. 1, the main body 1 comprises a pump unit 4 and a drive unit 3 for driving the pump unit. The pump unit 4 has a cylindrical casing 9. A suction port 7 for blood is formed in the proximal end portion of the casing 9, and a narrowed nozzle portion 6 is formed on the distal end portion of the casing 9. The casing 9 contains a propeller 23 which is formed on a propeller boss 24. Numeral 25 denotes a guide vane, and 26 denotes a guide vane boss which doubles as a flow regulator. The drive unit 3 has a liquid-tight casing 5, which contains a motor 30. The motor 30 serves to rotate the propeller 24 by means of its drive shaft 10. Thus, blood is sucked in through the suction port 7, and is delivered under pressure through the nozzle portion 6. The motor 30 is supplied with electric power from a power source (not shown).

An unidirectional dynamic-pressure bearing 22 is mounted on the distal end portion of the drive shaft 10 which is situated close to the propeller 24. The bearing 22 includes, for example, a cylindrical ceramic rotating member and a stationary member, and bears the drive shaft 10. Grooves formed on the peripheral surface of the rotating or stationary member allow a fluid in gaps between the members to be fed toward the propeller 24. Thus, the bearing 22 constitutes a dynamic-pressure sealing system. Moreover, a lip seal 27 of an elastic material, such as synthetic rubber, is provided on the propeller-side end of the bearing 22. The lip seal 27 also serves to maintain the sealing between blood and drive shaft 10.

Surrounding the drive shaft 10, a sealing solution chamber 21 is defined between the unidirectional dynamic-pressure bearing 22 and the motor 30. The chamber 21 is filled with the sealing solution, and communicates with a sealing solution bag 12 by means of a passage 31 and a flexible sealing solution tube 11. The sealing solution is fed from the bag 12 into the chamber 21. The sealing solution consists mainly of a physiological saline loaded with at least one of proteases or aminopeptides.

The artificial heart, constructed in this manner, is inserted or implanted in a heart A in the manner shown in FIG. 2. More specifically, an apical portion C of the heart A is cut open, and an apical ring 2 is embedded therein. The pump unit 4 of the main body 3 of the artificial heart is inserted into a left ventricle B. Numeral 8 denotes a sealing member. The nozzle portion 6 on the distal end portion of the pump unit 4 is inserted into an aorta E through an aortic valve D.

When the artificial heart is operated, blood in the left ventricle B is sucked in through the suction port 7 of the pump unit 4, and is fed through the nozzle portion 6 into the aorta E, bypassing aortic valve D. By doing this, the heart A is replenished with blood to make up for a deficiency which cannot be covered by natural heartbeats only. The sealing solution bag 12 is implanted in a body cavity outside the heart A.

As the drive shaft 10 rotates, the sealing solution in the sealing solution chamber 21 is delivered bit by bit toward the pump unit 4 by means of the unidirectional dynamic-pressure bearing 22. The sealing solution flows into the pump unit 4 via the lip seal 27. This flow of the sealing solution prevents blood in the pump unit 4 from getting into the space inside the lip seal 27 and the bearing 22.

EXAMPLE 1

In the artificial heart described above, the sealing solution bag 12, which communicates with the drive unit 3 by means of the sealing solution tube 11, is filled with a sealing solution which is formed of a physiological saline mixed with subtilisin, a protease, and a group of enzymes similar to subtilisin.

Subtilisin and the group of enzymes similar to subtilisin, which are proteases, have a wide variety of action characteristics and a positive proteolytic effect. Also, the half-life period of their activity in a solution is very long, ranging from 14 days to 21 days.

Since the sealing solution flows out from the bearing portion into blood at a low speed, the amount of enzymes released into the blood is very small, despite the relatively high enzyme concentration of the solution. The enzyme solution released from the bearing portion is diluted instantaneously by a bloodstream at a high rate of 3 to 5 liters per minute. The enzymes discharged into the blood are captured by $\alpha_1$-antiprotease, $\alpha_2$-macroglobulin, etc., and are quickly devitalized under the influence of phagocytosis by monocytes. Thus, hardly any side effect is produced.

Blood on the ventricle side of the heart of the human body is discharged from the suction port 7 of the casing 9 into the aorta through the nozzle portion 6 by means of an axial flow pump. The sealing solution filling the sealing solution chamber 21 which communicates with the sealing solution bag 12 is constantly released into the axial flow pump through the lip seal 27 by the agency of the dynamic-pressure generating grooves (not shown) of the unidirectional dynamic-pressure bearing 22. At the same time, coagulation of the blood in the bearing 22 can be positively restrained by the action of the proteases mixed with the sealing solution, and the bearing 22 can be cleaned. Accordingly, the drive shaft can be securely sealed against blood, so that it can be prevented from seizing, and therefore, can rotate without hindrance. Thus, the life performance of the blood pump can be improved considerably.

Since the sealing solution flowing out into the pump unit is very little, moreover, it exerts no influence upon the human body at all. The sealing solution, once loaded, need not be externally resupplied during a period of about one year or more.

EXAMPLE 2

In the artificial heart described above, the sealing solution bag 12, which communicates with the drive unit 3 by means of the sealing solution tube 11, is filled with a sealing solution which is formed of a physiological saline mixed with a protease named thermolysin, which is secreted by B-thermoproteolyticus, a thermoduric bacterium.

The thermoduric bacteria are germs which are alive at too high a temperature for the survival of ordinary bacteria, and are found in hot-spring water (70° to 80° C.) or the like.

The proteases secreted from the thermoduric bacteria have a very high resistance to heat, and their optimum working temperature is as high as 70° to 80° C.

The temperature in the bearing gap is as high as 50° to 70° C., and degenerative agglutination of fibrinogen attributable to this temperature constitutes a maximum cause of cohesion of the bearing.

Since the optimum working temperature of ordinary enzymes is as high as the bodily temperature, ranging from 36° to 40° C., so that these enzymes suddenly lose their effectiveness at the high temperature of 50° to 70° C. On the other hand, the proteases secreted from the thermoduric bacteria fulfill their maximum function at the high temperature in the bearing. At a temperature of 36° C. or thereabout, moreover, the function of these proteases can be maintained for two weeks or more, thus ensuring a prolonged effect.

According to an experiment, it was confirmed that the cohesion of the bearing in the fibrinogen solution can be fully prevented with use of a very low enzyme concentration of 10 µg/ml.

Further, epidermic cells cannot be damaged if the enzyme concentration is increased by 50 times (500 µg/ml). According to a report, blood contains $\alpha_2$-macroglobulin, whose molecules capture thermolysin, at a molar concentration 5,000 times as high as the daily dose (50 µg) of thermolysin.

Since the sealing solution flows out from the bearing portion into blood at a low speed, the amount of enzymes released into the blood is very small, despite the relatively high enzyme concentration of the solution. The enzyme solution released from the bearing portion is diluted instantaneously by a bloodstream at a high rate 3 to 5 liters per minute. The enzymes discharged into the blood are captured by $\alpha_2$-macroglobulin, and are quickly devitalized under the influence of phagocytosis by monocytes. Thus, hardly any side effect is produced.

EXAMPLE 3

In the artificial heart described above, the solution bag 12, which communicates with the drive unit 3 by means of the sealing solution tube 11, is filled with a sealing solution which is loaded with a plurality of kinds of aminopeptides. These aminopeptides constitute part of fibrinogen molecules, and serve to restrain the polymerization of fibrinogen and to increase the temperature at which fibrinogen monomer has its properties changed by heat.

The following is a description of the function of the aminopeptides loaded into the sealing solution.

Gly-Pro-Arg . . . for blocking the γ-chain C-terminal receptors was used as the sealing solution. Actually, an aminopeptide formed of four amino acids, glycine, proline, arginine, and proline, was used. The reason why the fourth amino acid is proline is that Gly-Pro-Arg-Pro is found to be able to be polymerized more firmly with the receptors than an aminopeptide formed of three amino acids, glycine, proline, and arginine, or Gly-Pro-Arg-Val, the original amino acid sequence of the A-α chains.

A shaft operation test was conducted using 100 ml of a fibrinogen solution (200 ml/dl: $0.6 \times 10^{-5}$M) loaded with 29 mg of Gly-Por-Arg-Pro (0.6×10$^{-3}$M). In a fibrinogen solution without Gly-Pro-Arg-Pro therein, the bearing suffered cohesion and stopped from rotating in 60 to 90 minutes. In the fibrinogen solution containing Gly-Pro-Arg-Pro, on the other hand, separation of the fibrins is restrained completely. Moreover, the time required before the shaft cohered and stopped from rotating greatly extended to 360 to 400 minutes.

While these aminopeptides are loaded into the shaft cleaning fluid, their respective concentrations are set in accordance with the speed at which fibrinogen from blood diffuses into the bearing. If the molar concentration of the aminopeptide is set at a value about one hundred times that of fibrinogen in the bearing, the polymerization of the fibrins in the bearing can be restrained completely.

Aminopeptides of Gly-Pro-Arg-Pro structure combine with the receptor of fibrinogen D domain, to increase the temperature at which the D domain has its properties changed by heat.

Originally, these aminopeptides constitute part of fibrinogen molecules, and are not noxious to organisms at all. Since the sealing solution flows out from the bearing portion into blood at a low speed, moreover, the rate of flow of the aminopeptides released into the blood is as low as 1 cc or less per hour, despite the relatively high aminopeptide concentration in the bearing. The sealing solution released from the bearing portion is diluted instantaneously by a bloodstream at a high rate of 3 to 5 liters per minute. For these reasons, coagulation systems of organisms can hardly be affected by the aminopeptides.

Figure 3:
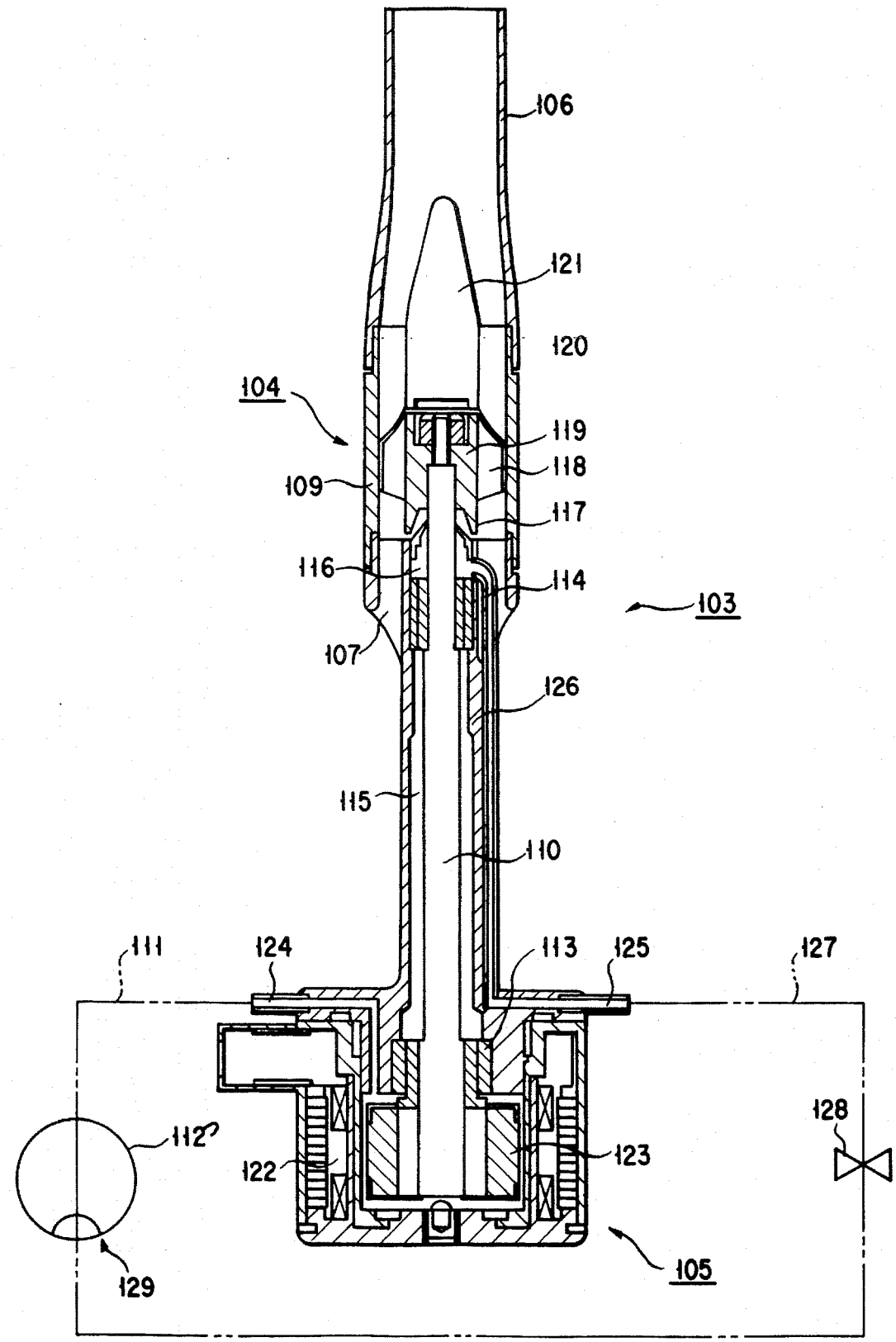
FIG. 3 is a longitudinal sectional view of an implant-type artificial heart according to another embodiment of the invention.

FIG. 3 shows an artificial heart according to another embodiment of the present invention. This artificial heart, like the aforementioned one, is an implant-type artificial heart.

In FIG. 3, numerals 104 and 105 denote a cylindrical pump unit and a drive unit for driving a built-in pump of the pump unit, respectively. Numeral 109 denotes a casing which has a nozzle portion on its distal end.

The proximal end portion of the pump unit 104 is connected to the drive shaft 110, and a plurality of suction ports 107 are arranged around an intermediate portion of the unit 104. The casing 109 is anchored to the outer periphery of the distal end portion of the pump unit 104.

The drive unit 105 contains a motor 122 which has a rotor 123. A drive shaft 110, which is connected to the motor 122, extends in the intermediate portion of the pump unit 104, and is connected to the pump. The proximal end portion of the drive shaft 110 is supported by means of a dynamic-pressure bearing 113. A suction port 124 and a discharge port 125 are arranged so that a sealing solution can be sucked in and discharged through them.

The motor 122 is a canned motor in which circulates the sealing solution sucked in through the suction port 124.

Disposed in the pump unit 104 is a unidirectional dynamic-pressure bearing 114, which bears the distal end portion of the drive shaft 110 and functions as a circulating pump. Surrounding the shaft 110, a sealing solution chamber 115 is defined between the dynamic-pressure bearings 113 and 114. Also, a fluid chamber 116 is defined between the bearing 114 and a sealing member 117 which seals the shaft to prevent introduction of blood from the pump. Further, a flow pipe 126 is provided so that the sealing solution can flow from the fluid chamber 116 to the discharge port 125 of the drive unit 105 through it. The sealing solution chamber 115 communicates with a sealing solution bag 112, which is implanted in the human body, by means of the suction port 124 of the drive unit 105 and a flexible delivery tube 111. The fluid chamber 116 communicates with the bag 112 by means of the flow pipe 126, the discharge port 125 of the drive unit 105, and a flexible return tube 127.

A propeller boss 119 and a guide vane boss 121 are arranged adjacent to each other in the casing 109. The propeller boss 119 is formed integrally with a propeller 118, and is mounted on the drive shaft 110 which constitutes the pump. The guide vane boss 121 is formed integrally with a guide vane 120. Blood in the ventricle of the heart is discharged into a nozzle portion 106 through the suction ports 107.

The blood in the ventricle of the heart is discharged from the suction port 107 of the casing 109 into the aorta through the nozzle portion 106 by means of the pump. The sealing member 117, such as an oil seal, is mounted on the drive shaft 110 of the motor for driving the pump, whereby blood from the pump side is shut out. On the other hand, the sealing solution flows out from and returns to the sealing solution bag 112 at a flow rate increased (to 1 cc/min or more) by the circulating-pump action of dynamic-pressure generating grooves (not shown) of the unidirectional dynamic-pressure bearing 114, circulating through the delivery tube 111, dynamic-pressure bearing 113, sealing solution chamber 115, fluid chamber 116, flow pipe 126, and return tube 127, in the order named.

The sealing solution, which is of the same kind as the ones used in Examples 1 to 3, serves to prevent coagulation of blood. According to this embodiment, the sealing solution circulates through the unidirectional dynamic-pressure bearing 114 at the high flow rate. In case blood gets into the bearing 114, therefore, it is diluted by the abundant sealing solution. Thus, the blood coagulation can be prevented more securely.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An artificial internal organ comprising:

a pump unit through which blood circulates, a driving unit for driving the pump unit, a driving shaft connecting the driving unit and the pump unit to each other, and driving shaft-sealing means for preventing the blood from flowing from the pump unit into the driving unit, said driving shaft-sealing means including:

a sealing member for sealing an outer circumference of the driving shaft;

a sealing solution chamber defined between the sealing member and the driving unit and surrounding the driving shaft, said sealing solution chamber being filled with a sealing solution;

a sealing solution bag containing the sealing solution and communicating with the sealing solution chamber by way of a supply tube and a return tube; and a unidirectional dynamic pressure bearing for rotatably supporting the driving shaft, said unidirectional dynamic pressure bearing including a rotor side member and a stator side member which are arranged in the sealing solution chamber and are slidable relative to each other, said sealing solution in the sealing solution chamber being supplied to the sealing member through a region defined between sliding surfaces of the rotor and stator side member, thereby circulating the sealing solution between the sealing solution bag and the sealing solution chamber, said sealing solution containing a protease or an aminopeptide or both.

2. An artificial internal organ according to claim 1, wherein said protease is selected from the group consisting of subtilisin, chymotrypsins A, B and C, acrosin, elastase, aspergillus alkaline proteinase, papain, bromelain, yeast proteinase, pronase and furin.

3. An artificial internal organ according to claim 1, wherein said protease is selected from the group consisting of caldolysin secreted by thermus T-351, aqualysin secreted by *thermus aquaticus,* protease secreted by B-caldolyticus, protease secreted by *streptomyces rectus* var proteolyticus, protease secreted by *T-caldophilus sp* n strain GK24, and thermolysin secreted by B-thermproteolyticus.

4. An artificial internal organ according to claim 1, wherein said aminopeptide constitutes part of a fibrinogen molecule.

5. An artificial internal organ according to claim 4 wherein said aminopeptide is a polypeptide formed of the four amino acids glycine, proline, arginine, and proline.

* * * * *